United States Patent
Morris et al.

(10) Patent No.: US 10,702,659 B2
(45) Date of Patent: Jul. 7, 2020

(54) DOSING ASSEMBLY FOR DRUG DELIVERY DEVICE WITH DIFFERENT LEADS AND MULTI-START THREAD SECTION

(71) Applicant: Sanofi, Paris (FR)

(72) Inventors: Anthony Paul Morris, Coventry (GB); Paul Griffin, Worcestershire (GB)

(73) Assignee: Sanofi, Paris (FR)

( * ) Notice: Subject to any disclaimer, the term of this patent is extended or adjusted under 35 U.S.C. 154(b) by 261 days.

(21) Appl. No.: 15/517,363

(22) PCT Filed: Oct. 9, 2015

(86) PCT No.: PCT/EP2015/073431
§ 371 (c)(1),
(2) Date: Apr. 6, 2017

(87) PCT Pub. No.: WO2016/055626
PCT Pub. Date: Apr. 14, 2016

(65) Prior Publication Data
US 2017/0304550 A1 Oct. 26, 2017

(30) Foreign Application Priority Data
Oct. 9, 2014 (EP) ..................................... 14306593

(51) Int. Cl.
*A61M 5/315* (2006.01)
*A61M 5/20* (2006.01)
*A61M 5/31* (2006.01)

(52) U.S. Cl.
CPC .......... *A61M 5/31541* (2013.01); *A61M 5/20* (2013.01); *A61M 5/2033* (2013.01);
(Continued)

(58) Field of Classification Search
CPC ................ A61M 5/20; A61M 5/31541; A61M 5/31553; A61M 5/31561; A61M 5/2033;
(Continued)

(56) References Cited

U.S. PATENT DOCUMENTS 5,308,340 A * 5/1994 Harris .................... A61J 1/1406
604/208
6,936,032 B1 * 8/2005 Bush, Jr. ........... A61M 5/31551
604/187
(Continued)

FOREIGN PATENT DOCUMENTS

WO WO 2010/053569 * 5/2010
WO WO 2010/139645 12/2010
(Continued)

OTHER PUBLICATIONS

International Search Report and Written Opinion in International Application No. PCT/EP2015/073431, dated Jan. 1, 2015, 14 pages.
(Continued)

*Primary Examiner* — Theodore J Stigell
(74) *Attorney, Agent, or Firm* — Fish & Richardson P.C.

(57) ABSTRACT

The present invention is generally directed to an assembly for a drug delivery device comprising a first threaded member (50, 50'), a second threaded member (40, 60') with a longitudinal axis and a thread (61), having at least two consecutive portions (62, 63, 64) with different leads. The first threaded member (50, 50') and the second threaded member (40, 60') are adapted and arranged to rotate with respect to one another about the longitudinal axis of the second threaded member (40, 60') during dose setting operation of the assembly, the first threaded member (50, 50') thereby being axially displaced along the second threaded member (40, 60') from a start position to an end position with respect to the second threaded member (40, 60') due to the mechanical cooperation of the first threaded member (50,
(Continued)

50') with the thread (61). According to the invention, a fast portion (62, 64) of the thread (61), having a greater lead than a slow portion (63) of the thread (61), comprises a multi-start thread and the slow portion (63) comprises less starts than the fast portion (62, 64). The invention is further directed to a drug delivery device for setting and dispensing a number of user variable doses of a medicament comprising such an assembly.

15 Claims, 7 Drawing Sheets

(52) U.S. Cl.
CPC .... *A61M 5/31553* (2013.01); *A61M 5/31561* (2013.01); *A61M 5/31583* (2013.01); *A61M 2005/3126* (2013.01); *A61M 2205/581* (2013.01); *A61M 2205/582* (2013.01); *A61M 2205/583* (2013.01)

(58) Field of Classification Search
CPC ...... A61M 2005/3126; A61M 5/31583; A61M 5/31593; A61M 5/31551
See application file for complete search history.

(56) References Cited

U.S. PATENT DOCUMENTS

| | | |
|---|---|---|
| 2006/0153693 A1 | 7/2006 | Fiechter et al. |
| 2010/0324494 A1* | 12/2010 | Plumptre .......... A61M 5/31551 604/207 |
| 2019/0134312 A1* | 5/2019 | Fumiyama .......... A61M 5/3129 |
| 2019/0134313 A1* | 5/2019 | Baxter .................... A61M 5/20 |

FOREIGN PATENT DOCUMENTS

| | | |
|---|---|---|
| WO | WO 2013/010884 | 1/2013 |
| WO | WO 2014/111335 | 7/2014 |

OTHER PUBLICATIONS

International Preliminary Report on Patentability in International Application No. PCT/EP2015/073431, dated Apr. 11, 2017, 10 pages.

\* cited by examiner

DOSING ASSEMBLY FOR DRUG DELIVERY DEVICE WITH DIFFERENT LEADS AND MULTI-START THREAD SECTION

CROSS-REFERENCE TO RELATED APPLICATIONS

This application is a U.S. national stage application under 35 USC § 371 of International Application No. PCT/EP2015/073431, filed on Oct. 9, 2015, which claims priority to European Patent Application No. 14306593.6, filed on Oct. 9, 2014, the entire contents of which are incorporated herein by reference.

The present invention is generally directed to an assembly for a drug delivery device and to a drug delivery device for selecting (setting) and dispensing a number of user variable doses of a medicament comprising such an assembly.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place.

While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

WO 2010/139645 A1 discloses a dose setting mechanism for a drug delivery device comprising a shaft with a helical groove having a first portion with a first pitch and a consecutive second portion with a second pitch, which is different from the first pitch. A nut which has a twin-start thread engages the shaft. Further, the nut is in splined engagement with a housing to prevent relative rotation of the nut and the housing. The shaft and the nut are part of a last dose mechanism preventing a user from setting a dose that is greater than the amount of medication remaining in the cartridge.

Certain aspects of the present disclosure relate to an improved threaded assembly, e.g. for a last dose mechanism of a drug delivery device.

According to the invention, the assembly comprises a first threaded member and a second threaded member with a longitudinal axis comprising a thread which comprises at least two consecutive portions with different leads. The first threaded member and the second threaded member are adapted and arranged to rotate with respect to one another about the longitudinal axis of the second threaded member during dose setting operation of the assembly, whereby the first threaded member is axially displaced along the second threaded member from a start position to an end position with respect to the second threaded member due to the mechanical cooperation of the first threaded member with the thread. A fast portion of the thread, which is a portion having a greater lead than a slow portion of the thread, comprises a multi-start thread and the slow portion comprises fewer starts than the fast portion. Providing regions with a different lead allows adapting the respective lead to individual requirements of the region. For example, if the axial length of one of the threaded members is to be limited, the slow portion may be used for reducing the overall length. On the other hand, if a robust rotational hard stop with relatively large abutment faces is desired, a fast portion may be provided at the stop. In other words, fast and slow portions of the thread may be located in regions of the respective thread member requiring such thread properties.

The term "lead" is defined as the distance along a screw axis that is covered by one complete rotation (360°) of the screw. In contrast to that the term "pitch" is defined as the distance from the crest of one thread to the next thread crest. In single-start thread-forms, their lead and pitch are the same. "Single-start" means that there is only one ridge or groove wrapped around the cylinder of the screw body. Each time that the screw body rotates one turn (360°), it advances axially by the width of one ridge or groove. The terms "double-start" or "multiple-start" mean that there are two or multiple ridges or grooves wrapped around the cylinder of the screw body. Each time that the screw body rotates one turn (360°), it advances axially by the width of two or multiple ridges or grooves. In other words, lead and pitch are parametrically related by the number of starts. In general, lead is equal to pitch times the number of starts.

One of the thread members may have the form of a (shorter) threaded nut, whereas the other of the thread members may have the form of a (relatively longer) screw. As an alternative, the nut member may be a (relatively longer) threaded sleeve, while the screw member may be shorter. Preferably, it is the screw member which has the portions with a different lead, while the nut member has a thread form fitting to the different leads of the screw member.

A start position may be a position, at which a defined relative movement of the threaded members begins, whereas the end position may be a position, at which a defined relative movement of the threaded members terminates, e.g. by an end stop. In a preferred embodiment of the invention the start position is a start position of a last dose mechanism, i.e. the relative position of two component parts corresponding to a full (fresh) cartridge, while the end position is an end position of a last dose mechanism, i.e. the relative position of two component parts corresponding to an empty cartridge. Neither the start position nor the end position has to be at an end of the respective threaded member. However, it is preferred that at least one of the start position and the end position is located at an end of a threaded member. Preferably, the thread of the second threaded member terminates at the end position in a rotational hard stop.

The first threaded member preferably comprises thread protrusions which are inclined with respect to the longitudinal axis of the assembly such that their slope allows them to be guided in the fast thread portions. Further, two opposite angles of the thread protrusions are preferably truncated (complanated) such that the slope of the truncated regions allows them to be guided in the slow thread portion of the second threaded member. In other words, a thread protrusion engages the thread on the second threaded member with a different surface depending on the thread protrusion engaging either a slow thread portion or a fast thread portion.

Preferably, the first threaded member engages the slow portion of the thread when the first threaded member is at the start position of the second threaded member, wherein the first threaded member engages the fast portion of the thread when the first threaded member is at the end position of the second threaded member.

As an alternative, the first threaded member engages a first fast portion of the thread when the first threaded member is at the start position of the second threaded member, wherein the first threaded member engages a second fast portion of the thread when the first threaded member is at the end position of the second threaded member, and wherein the first threaded member engages the slow portion of the thread when the first threaded member is at a center position of the second threaded member, which center position is located between the start position and the end position along the longitudinal axis of the second threaded member.

In a preferred embodiment, the fast portion of the thread comprises a twin-start thread and the slow portion comprises a single-start thread.

In addition to the different number of starts of the respective portions of the thread, they may vary regarding their pitch. For example, the fast portion of the thread has a greater pitch than the slow portion of the thread. The combined effect of the number of starts and the variation in pitch may result in the ratio of the lead of the fast portion of the thread to the lead of the slow portion of the thread being above 1:1 and equal to or below 10:1, preferably 5:1.

If the lead of a threaded engagement is too large, it is possible that the thread is not self-locking, i.e. the two threaded members may move relative to each other under the action of an axial force, like gravity. This may be undesired for example during assembly of a device, when the threaded members are in engagement but should not move relative to each other unintended. In such cases, the thread of the second threaded member may comprise an assembly location feature at or near the start position. Such an assembly location feature may be a protrusion provided on the base or a side wall of a thread groove or a variation in the width or depth of a thread groove or ridge which prevents nut movement caused by gravity or by an axial force but which is easily overcome when a torque is applied.

The assembly may further comprise a third member, e.g. a sleeve, which is adapted and arranged to axially guide the first threaded member and which is rotationally constrained to the first threaded member. In other words, relative rotation of the second member to the third member causes the first member to axially advance relative to the second member and/or the third member. In a preferred embodiment of the invention, the three members constitute a last dose mechanism of a drug delivery device, with the second member and the third member e.g. rotating relative to each other during dose setting, thus advancing the first member, and not rotating relative to each other during dose dispensing, thus not advancing the first member.

Preferably, the first threaded member comprises at least a first thread form protrusion and a second thread form protrusion instead of a single, continuous thread protrusion. The thread form protrusions extend about an angle of less than 180° each and are arranged such that the thread form protrusions both engage the same helical thread groove of the second threaded member when engaging a single-start thread portion. In other words, one of the protrusions is a leading protrusion and the other protrusion is following this leading protrusion in the same track. Further, the thread form protrusions preferably engage different helical thread grooves of the second threaded member when engaging a multiple-start thread portion. Thus, when engaging a twin-start thread portion each of the two thread form protrusions are leading protrusions in different tracks. Each of these thread form protrusions may have similar formed trailing thread form protrusions located behind the respective leading thread form protrusion when seen in the direction of movement, i.e. the first threaded member may also comprise third and fourth thread form protrusions. The first and third thread form protrusions may then engage one helical thread groove and the second and fourth thread form protrusions may engage another helical thread groove when engaging a multiple-start thread portion of the second threaded member. The transition between a fast portion and a slow portion of the thread is preferably such that one of the thread form protrusions may engage the fast portion while the other of the thread form protrusions already engages the slow portion or vice versa.

According to the invention, a drug delivery device for setting and dispensing a number of user variable doses of a medicament comprises the above mentioned thread assembly and a cartridge containing a medicament. The drug delivery device may further comprise a housing, wherein the second threaded member and the housing perform a relative rotation during dose setting and do not rotate relative to each other during dose dispensing. If the device further comprises the third member, this third member is preferably rotationally constrained to the housing or is a unitary component part of the housing.

The second threaded member may be a drive sleeve which is coupled to a piston rod and which is rotated with respect to the housing during dose setting and which moves axially with respect to the housing or is stationary with respect to the housing during dose dispensing.

In a drug delivery device comprising the third member, wherein the second threaded member may be a dial sleeve which is coupled to a dose setting member and which is rotated with respect to the third member during dose setting and which is not rotated relative to the third member, e.g. it rotates together with the third member or is stationary with the third member, during dose dispensing.

Preferably, the drug delivery device comprises a last dose protection mechanism for preventing the setting of a dose, which exceeds the amount of liquid left in a cartridge, with the first member, the second member and, optionally, the third member constituting the last dose protection mechanism. This has the advantage that the user knows how much will be delivered before starting the dose delivery. It also ensures that dose delivery stops in a controlled manner without the bung entering the neck portion of the cartridge where the diameter is smaller which may result in an underdose. For example, if the last dose protection mechanism comprises a nut member interposed between the drive member and any other component which rotates during dose setting and dose dispensing, the nut member only moves axially during dose setting and remains stationary with respect to this component during dose dispensing. The nut member may be a full nut or a part thereof, e.g. a half nut.

The device may comprise a clutch operationally positioned between the drive member and the dose setting member. Preferably, the clutch rotationally de-couples the drive member and the dose setting member during dose setting and rotationally couples the drive member and the dose setting member during dose dispensing.

In a further development of this embodiment, the clutch between the dose setting member and the drive member is a slipping clutch with first clutch teeth on the drive member and second clutch teeth on a clutch sleeve, which is rotationally constrained to the dose setting member during dose setting and dose dispensing. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the bias of a clutch spring by allowing the sleeve and/or the clutch element to translate axially against the force of the clutch spring. This may result in an oscillating axial movement of the sleeve and/or the clutch element due to continued disengagement and following re-engagement into the next detented position. An audible click may be generated by this re-engagement, and tactile feedback may be given by the change in torque input required.

Preferably, the clutch between the drive member and the dose setting member is a slipping clutch which allows relative rotation between the drive member and the dose setting member in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

If the device has no dial extension, i.e. has a constant length irrespective of the size of the dose set, handling may be more user-friendly. In addition, this may make the device more reliable by preventing ingression of dirt or the like. For a device without dial extension, the dose setting member and/or the drive member may be axially constrained to the housing.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

The device may further comprise a piston rod which is in permanent threaded engagement with the housing or a housing insert. For example, the housing or insert may comprise an inner thread engaging an outer thread of the piston rod, while the drive member is rotationally constrained to and axially movable relative to the piston rod.

In another preferred embodiment, the drug delivery device further comprises a gauge element radially interposed between the outer housing and the dose setting element. The gauge element is axially movable relative to the outer housing and in threaded engagement with the dose setting element. The outer housing may comprise at least one aperture and the gauge element may comprise at least one aperture. If the dose setting element is a number sleeve which comprises markings on its outer surface, at least one of the markings is visible through the aperture in the gauge element and the aperture in the outer housing during dose setting and dose dispensing. The term aperture may include a simple opening the outer housing or gauge element or a transparent window or lens. A window in the outer housing may be incorporated using a 'twin-shot' moulding technology. For example, the outer housing is moulded during a 'first shot' in a translucent material, and the outer cover of the outer housing is moulded during a 'second shot' in an opaque material.

The gauge element may be axially guided within the outer housing such that rotation of the dose setting element causes an axial displacement of the gauge element. The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the outer housing. The gauge element may have the form of a shield or strip extending in the longitudinal direction of the device. As an alternative, the gauge element may be a sleeve. In an embodiment of the invention, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow view only on a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the outer housing and relative to the outer housing. In other words, the dose setting element does not perform a translational movement during dose setting. This prevents that the dose setting element is wound out of the outer housing or that the outer housing has to be prolonged for covering the dose setting element within the outer housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The injection device may comprise at least one clicker mechanism for generating a tactile and/or audible feedback. A feedback may be generated during dose setting (increasing and/or decreasing a dose), dose dispensing and/or at the end of dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(0)14 Trp(02)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\epsilon$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region (CH) and the variable region (VH). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Non-limiting, exemplary embodiments of the invention will now be described with reference to the accompanying drawings, in which:

FIG. 2 shows an exploded view of the components of the device of FIG. 1a;

Figure 3:
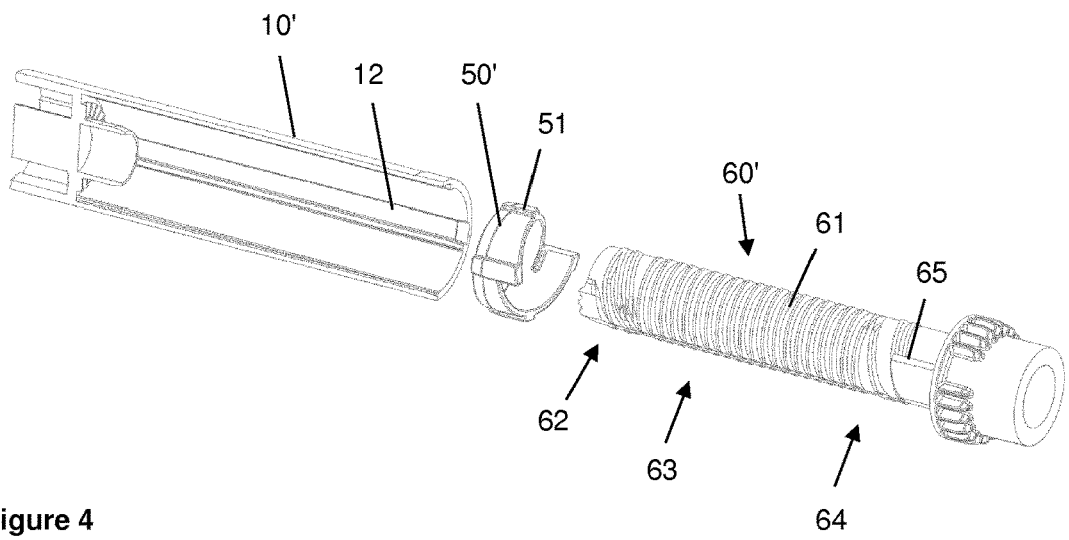
FIG. 3 shows an exploded view of the components of an assembly according to a second embodiment of the invention.
Figure 4:
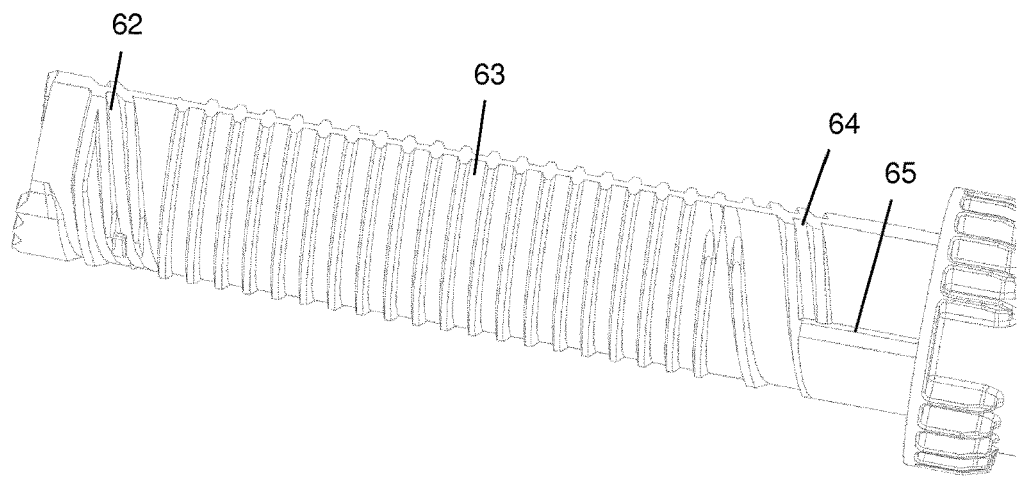
FIG. 4 shows a top view of the dial tube of the assembly of FIG. 3.
Figure 5A:
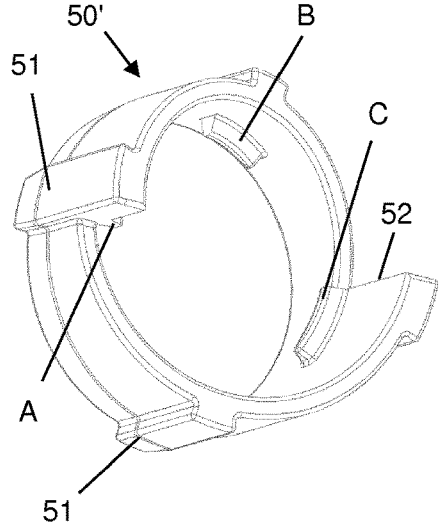
Figure 5B:
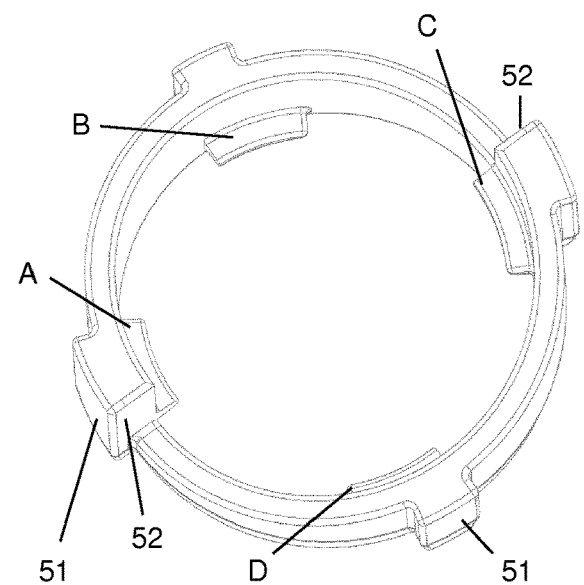
Figure 6:
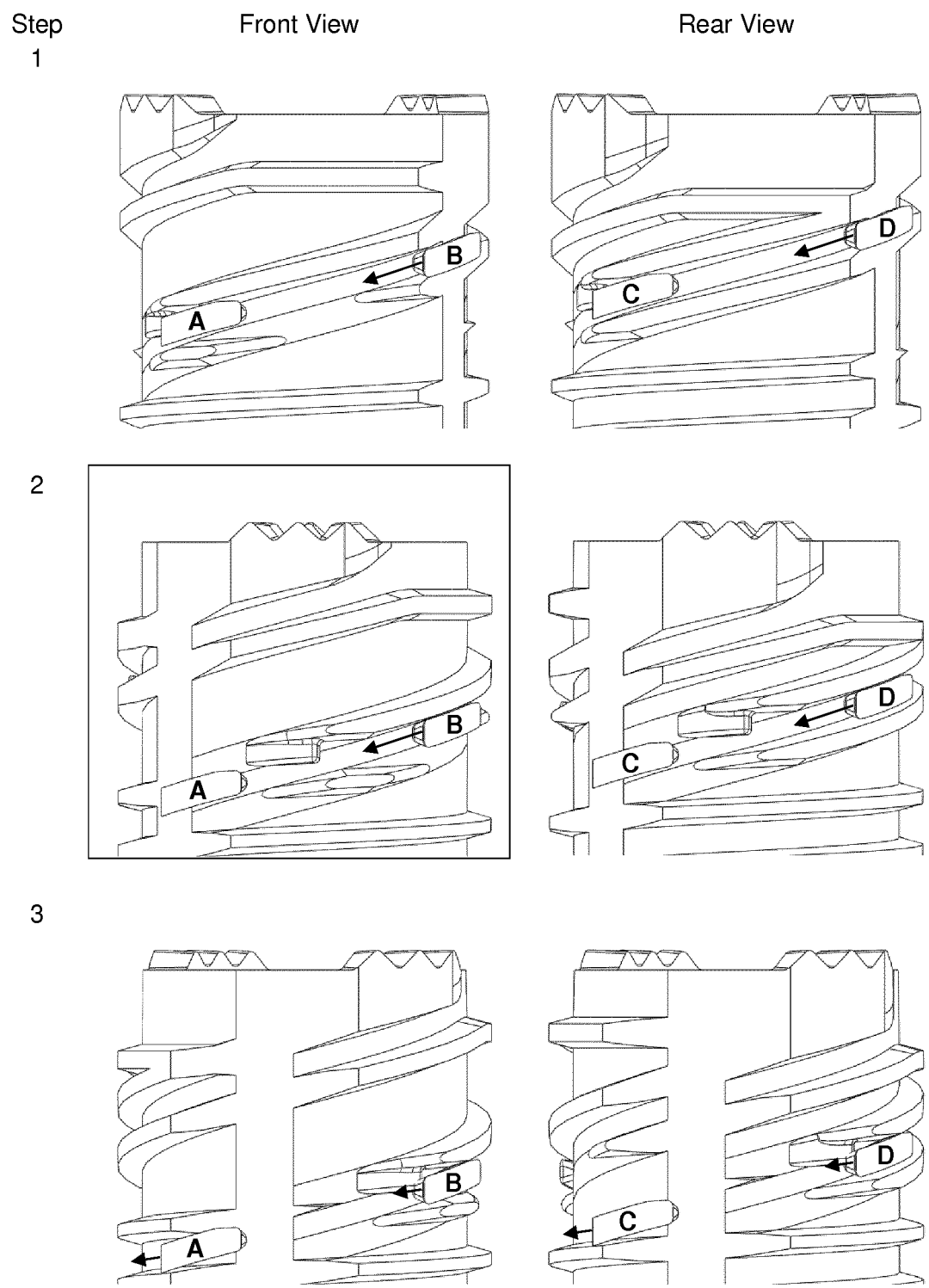
Figure 6:
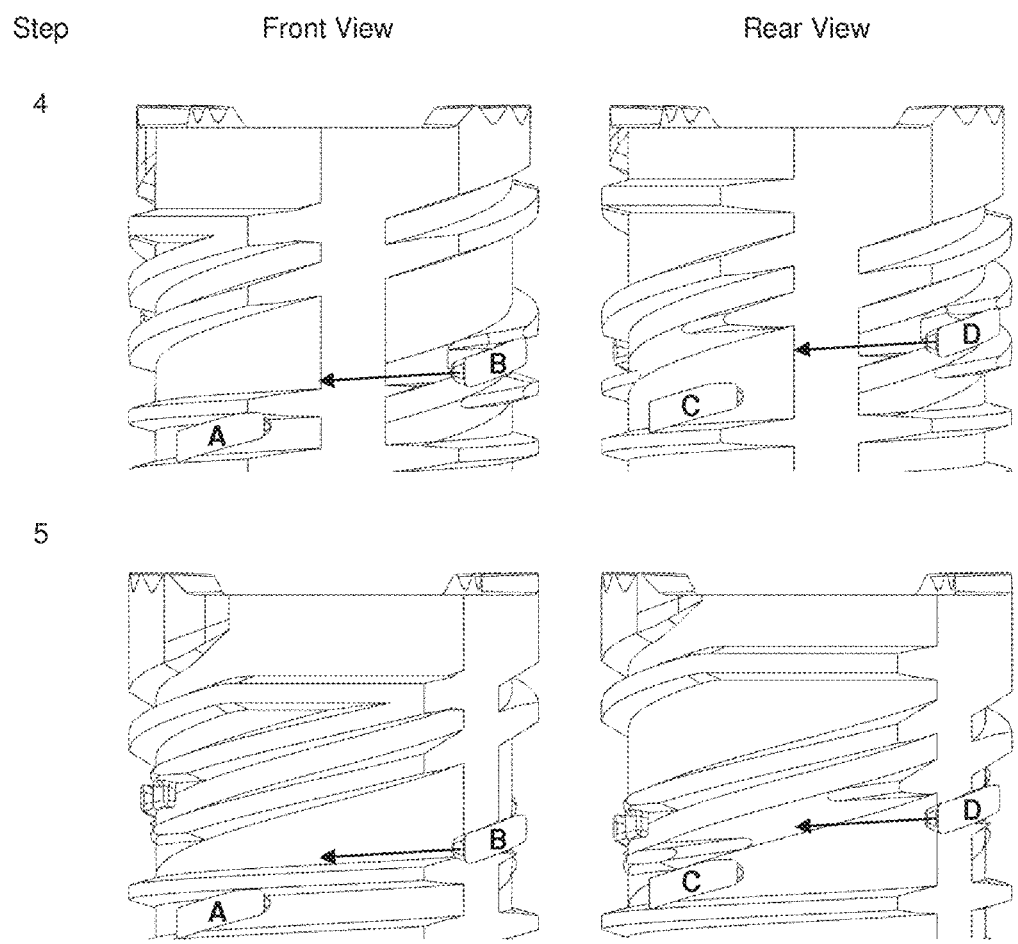
Figure 7:
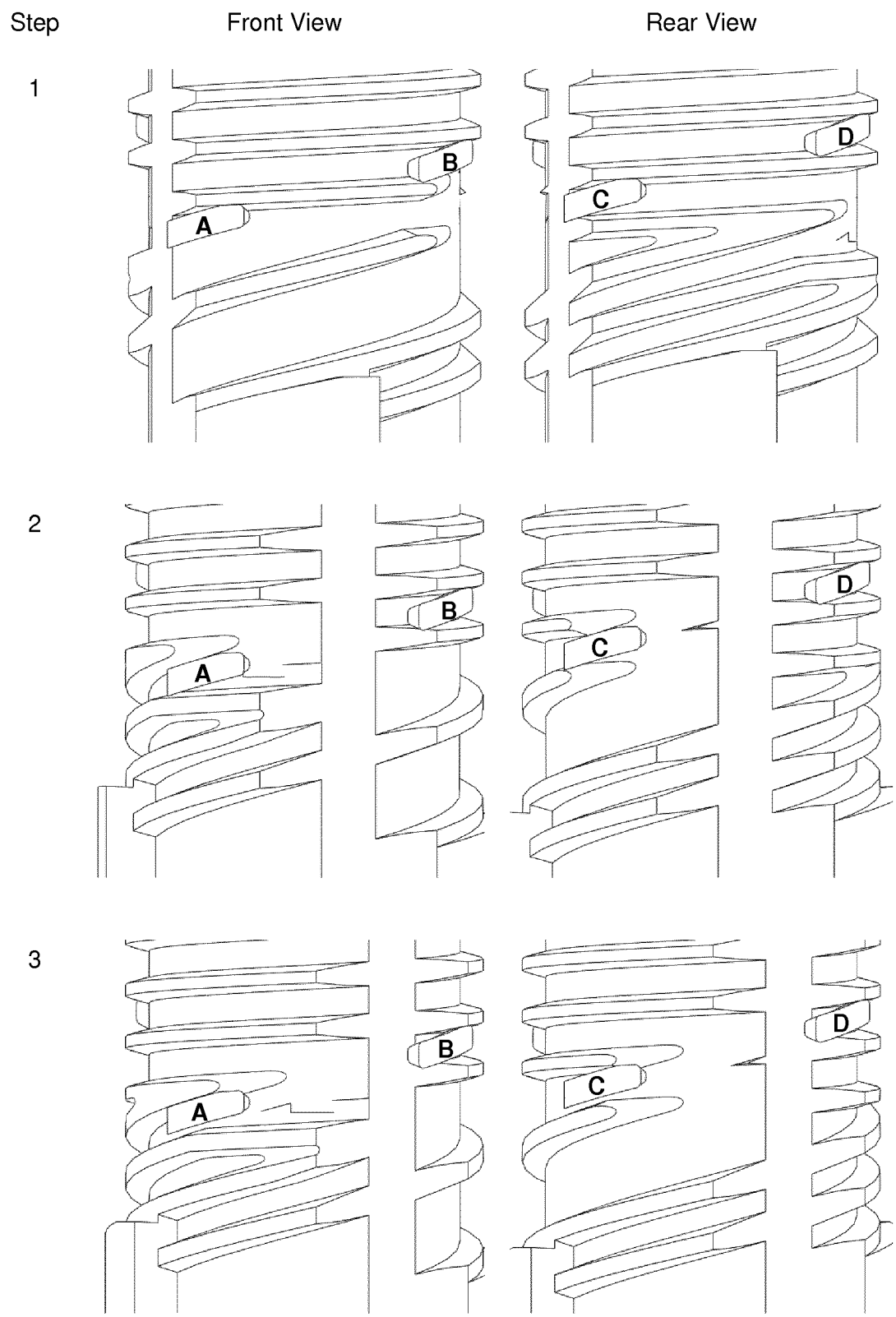
Figure 7:
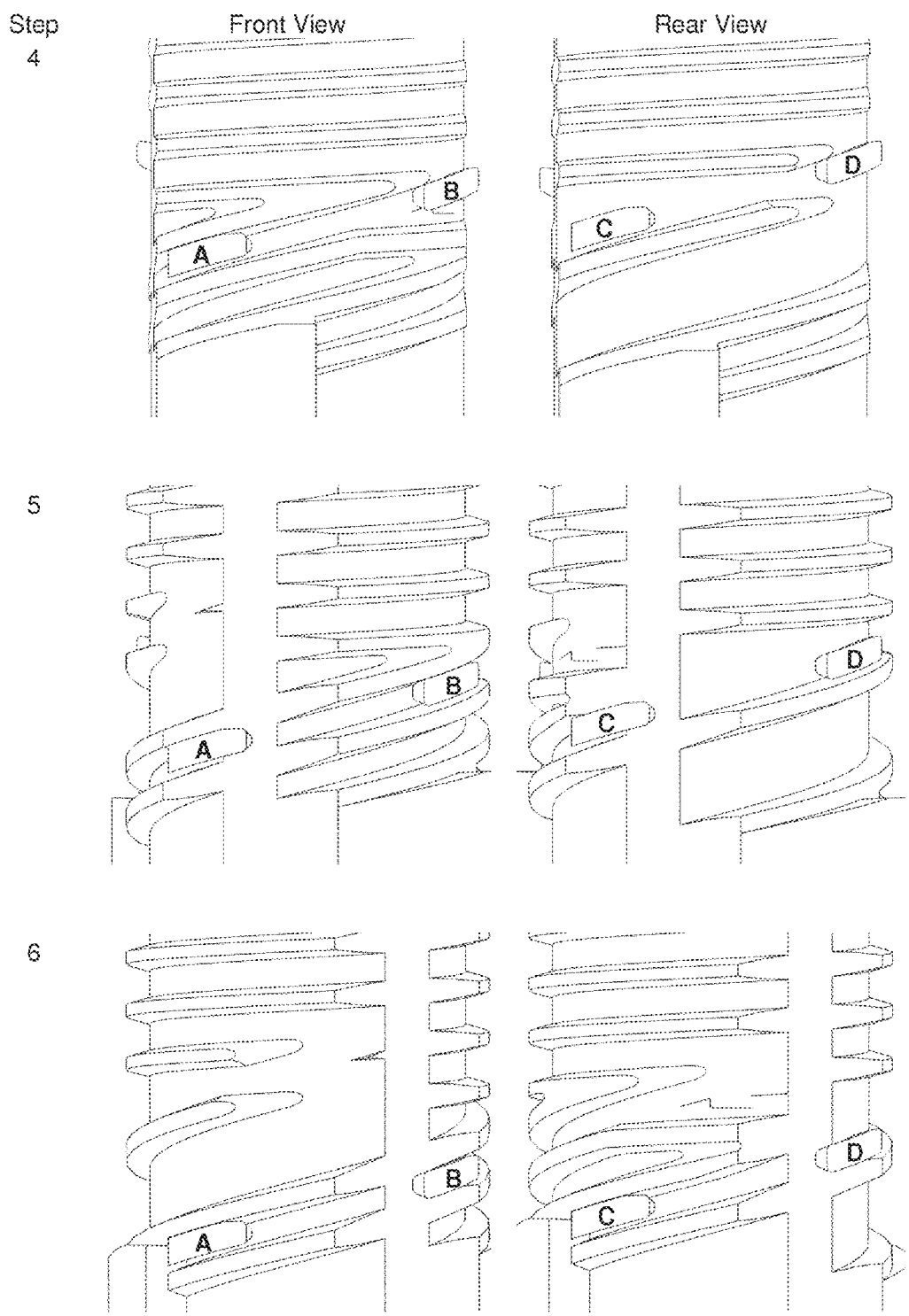
Figure 8A:
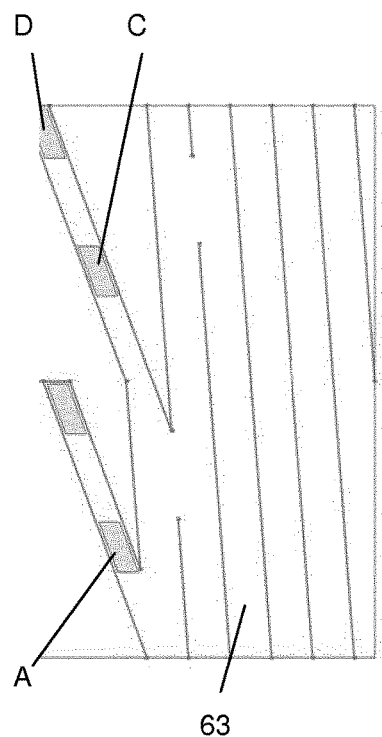
Figure 8B:
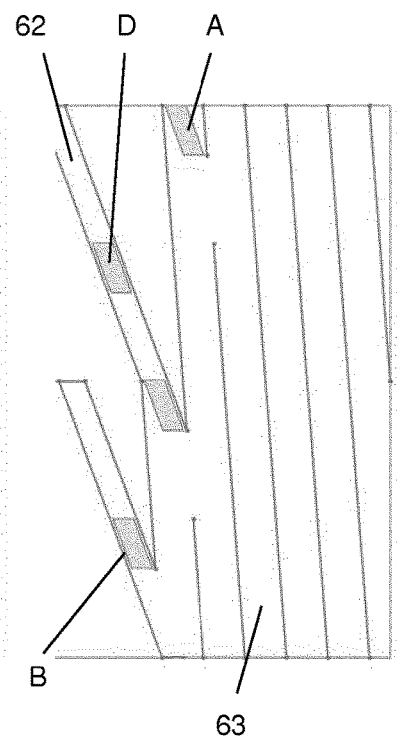
Figure 8C:
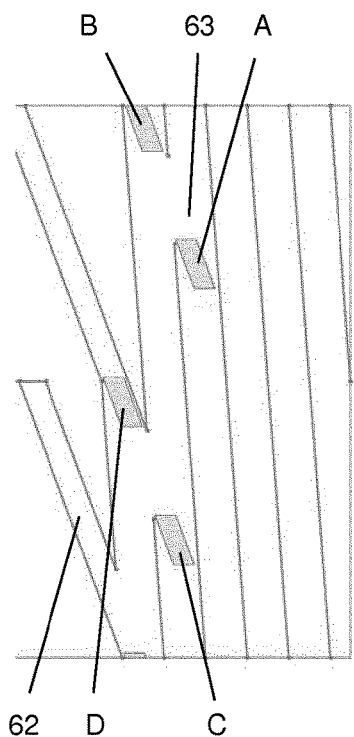
Figure 8D:
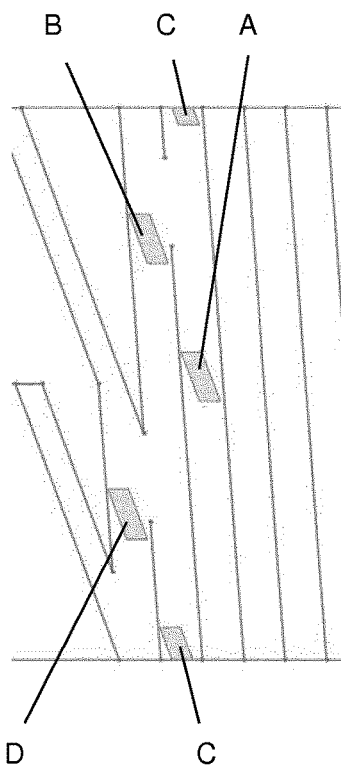
Figure 8E:
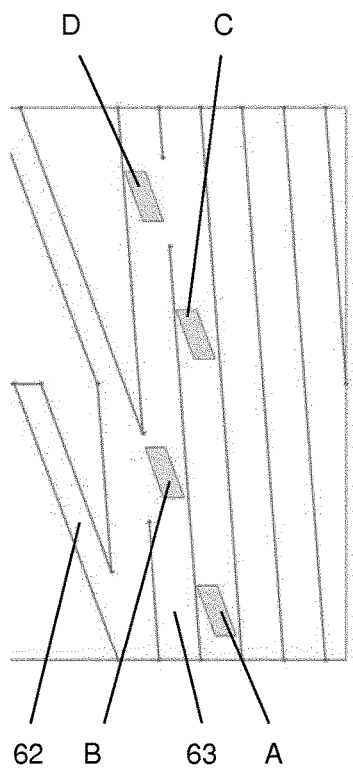
Figure 8F:
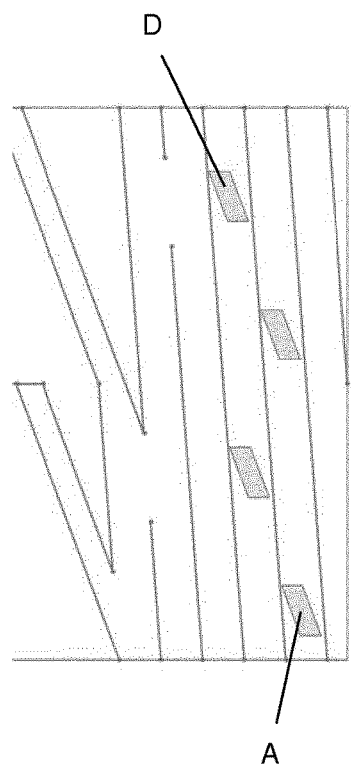

FIGS. 5a, b show views of the last dose nut of the assembly of FIG. 3;

FIG. 6 shows in a partly cut-away front and rear view the transition from a fast thread to a slow thread of the assembly of FIG. 3;

FIG. 7 shows in a partly cut-away front and rear view the transition from a slow thread to a fast thread of the assembly of FIG. 3; and FIGS. 8a-f show in flat projections the transition from a fast thread to a slow thread of the assembly of FIG. 3.

Figure 1A:
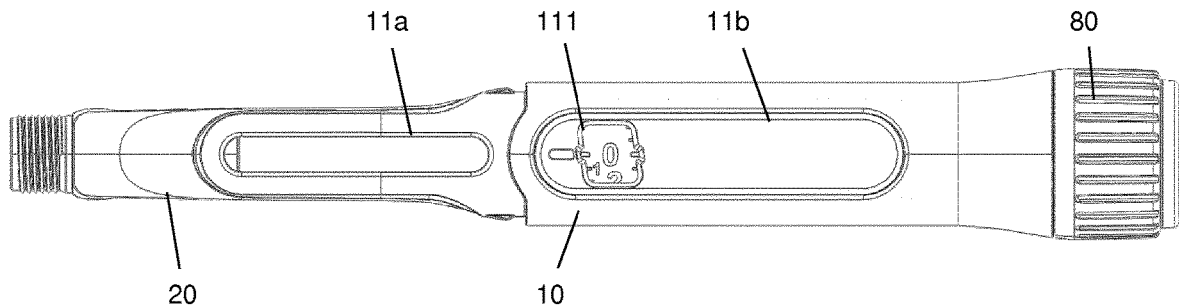
FIG. 1a shows a top view of the drug delivery device of a first embodiment of the present invention in the minimum dose position.
Figure 1B:
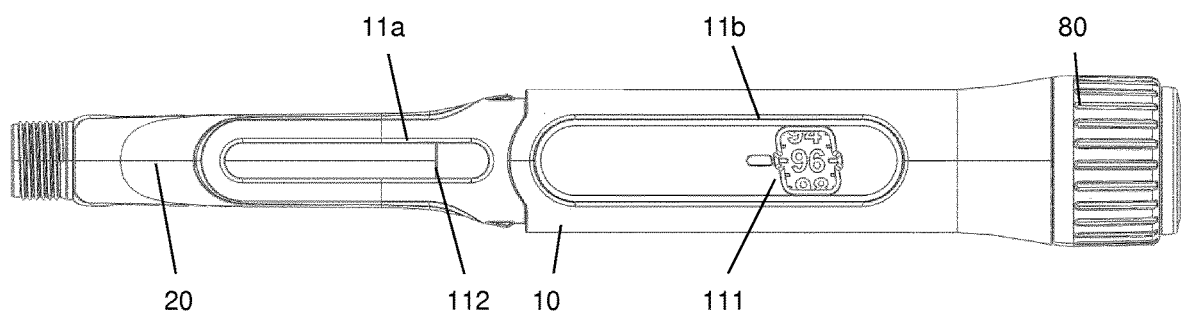
FIG. 1b shows a top view of the drug delivery device of FIG. 1a with a dose of 96 units dialled.
Figure 2:
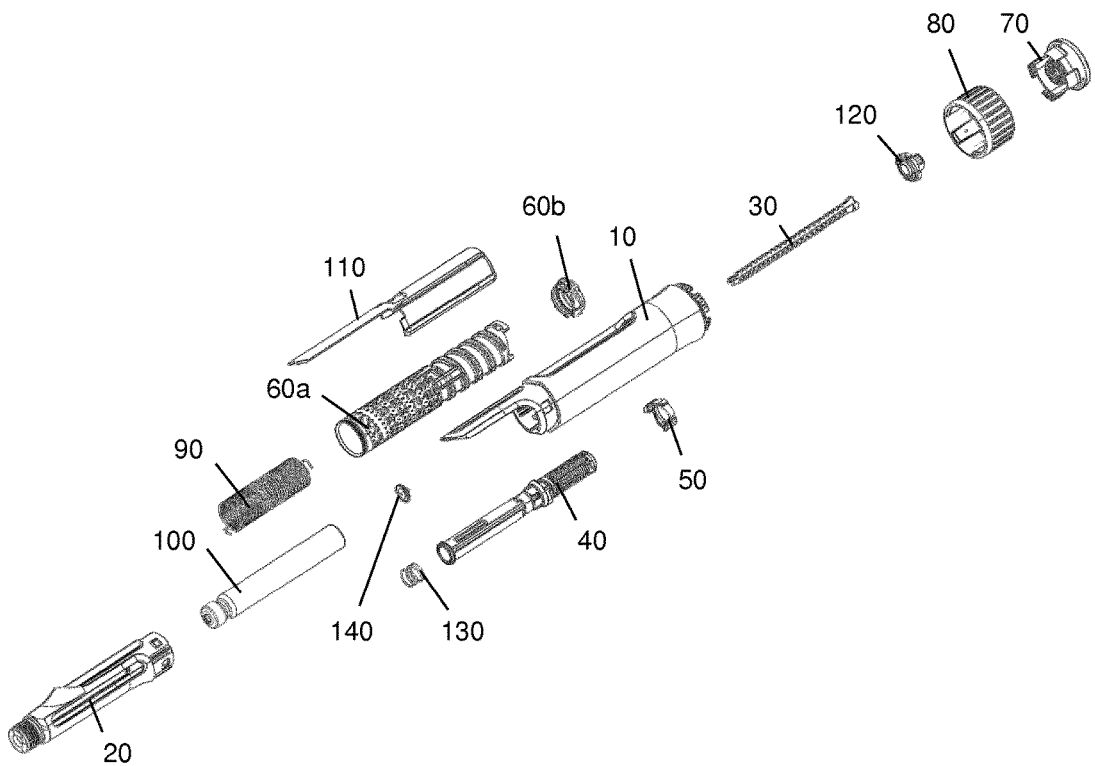

FIG. 1 shows a drug delivery device in the form of an injection pen. The device has a distal end (left end in FIG. 1a) and a proximal end (right end in FIG. 1a). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis of the mechanism.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. A flange-like or cylindrical inner wall comprises an inner thread engaging the piston rod 30. The housing 10 further has at least one internal, axially orientated slot or the like for axially guiding the gauge element 110. In the embodiment shown in the Figures, the distal end is provided with an axially extending strip partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the inner wall of housing 10. The lead screw 30 is an elongate member with an outer thread engaging the corresponding thread of the inner wall of housing 10. The thread may have a large lead-in, for example a wedge shape form, at its distal end to engage a corresponding housing thread form on the first rotation. The interface comprises at least one longitudinal groove or track and a corresponding protrusion or spline of the driver 40. At its distal end, the lead screw 30 is provided with an interface for clip attachment of the bearing 140. In the present embodiment, this interface comprises two clip arms extending in the distal direction defining an insertion space between them for insertion of a bearing 140 interface. As an alternative, the interface may comprise only one single clip arm extending more than 180° about the longitudinal axis, or may comprise one or several clip arms. The clip arm(s) may have a bent form with a recessed clip portion. Preferably, the clip arm(s) form a cylindrical outer face having a diameter equal to or smaller than the outer diameter of the lead screw 30 at the base of the groove (flute base) of the outer thread. A concave contact surface may be provided between the clip arms for abutment of a corresponding portion of bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing 10 prevents rotation of the drive sleeve 40 during dose setting. This interface comprises e.g. a ring of radially extending outer teeth at the distal end of drive sleeve 40 and corresponding radially extending inner teeth of the housing component 10. When the button 70 is pressed, these drive sleeve 40 to housing 10 spline teeth are disengaged allowing the drive sleeve 40 to rotate relative to housing 10.

A further splined tooth interface with the number sleeve 60 is not engaged during dialling, but engages when the button 70 is pressed, preventing relative rotation between the drive sleeve 40 and number sleeve 60 during dispense. This interface may comprise inwardly directed splines on a flange on the inner surface of the number sleeve 60 and a ring of radially extending outer splines of drive sleeve 40. The corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines are arranged such that they are decoupled when teeth of drive sleeve 40 and inner teeth of housing component 10 mesh and engage when teeth and inner teeth disengage. In a preferred embodiment the splines are longer in the axial direction compared with teeth. This allows engagement of the splines shortly before disengagement of teeth. In other words, the splines and the teeth are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines. As an alternative to the corresponding splines teeth may be provided. As a further alternative or in addition to splines, drive sleeve 40 and number sleeve 60 may be rotationally coupled to each other during dose dispensing via clutch plate 120.

An interface of the drive sleeve 40 comprises a ring of ratchet teeth located at the proximal end face of drive sleeve 40 and a ring of corresponding ratchet teeth of clutch plate 120.

The driver 40 has a threaded section (right hand side in FIG. 2) providing a helical track for the nut 50. In addition, a last dose abutment or stop is provided which may be the end of the thread track or preferably a rotational hard stop for interaction with a corresponding last dose stop of nut 50, thus limiting movement of the nut 50 on the thread of the drive sleeve 40. At least one longitudinal spline of the drive sleeve 40 engages a corresponding track of the lead screw 30. Further, the drive sleeve is provided with a ramp interacting with a clicker arm when the drive sleeve 40 is in its distal position during dose dispensing, i.e. when button 70 is depressed.

The last dose nut 50 is located between the number sleeve 60 and the drive sleeve 40. It is rotationally constrained to the number sleeve 60, via a splined interface including splines on nut 50. It moves along a helical path relative to the drive sleeve 40, via a threaded interface, when relative rotation occurs between the number sleeve 60 and drive sleeve 40 which is during dialling only. As an alternative, the nut 50 may be splined to the driver 40 and threaded to the number sleeve 60. In the embodiment shown in the Figures, the nut 50 is a full nut, but in alternative embodiments it may be a half nut, i.e. a component extending approximately 180° around the center axis of the device. A last dose stop is provided engaging stop of drive sleeve 40 when a dose is set corresponding to the remaining dispensable amount of medicament in the cartridge 100.

Although not shown in FIGS. 1a to 2 in detail, the threaded interface between the drive sleeve 40 and the nut 50 is designed such that the thread lead at the start and at the end of the thread of drive sleeve 40 is greater (fast thread) than in the central region (slow thread). In addition, both fast thread portions are a twin-start form whereas the slow thread is a single-start form. In this embodiment, the ratio between the fast and slow thread leads is 5:1, however, this exact ratio is not an absolute requirement. The inner thread of the nut may comprise several, for example four, thread ridge portions which are spaced from each other and distributed about the inner circumference of the nut. The thread ridge portions of the nut 50 engage the different thread portions of drive sleeve 40. In a transition phase during movement of the nut 50 relative to drive sleeve 40, some of the thread ridge portions of the nut 50 may engage a fast thread portion of the drive sleeve 40, while other thread ridge portions of the nut 50 may engage a slow thread portion of the drive sleeve 40. The design of this threaded assembly is preferably as described below in more detail with respect to the embodiment of FIGS. 3 to 8.

The dose indicator or number sleeve 60 is a tubular element as shown in FIG. 2. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in FIG. 2 comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60a is marked with a sequence of numbers, which are visible through the gauge element 110 and the openings 11a, 11b in the housing 10, to denote the dialled dose of medicament.

Further, the number sleeve lower 60a has a portion with an outer thread engaging the gauge element 110. End stops are provided at the opposite ends of this thread to limit relative movement with respect to the gauge element 110.

Clutch features which have the form of a ring of splines are provided inwardly directed on number sleeve upper 60b for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60a is rotationally constrained to the nut 50 and to the clutch plate 120 via a splined interface comprising at least one longitudinal spline.

An interface for attachment of the torsion spring 90 to the number sleeve lower 60a comprises large lead-ins and a groove feature with a pocket or anchor point for receiving a first coil or hook portion of the spring. The groove has an end feature in the form of a ramp that is in interference with the hook portion of the spring. The design of the groove is such that the spring 90 may be received within the pocket without interfering with the gauge element 110.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60b. Thus, the button is also splined via splines to the number sleeve upper 60b when the button 70 is not pressed, but this spline interface is disconnected when the button 70 is pressed. The button 70 has a discontinuous annular skirt with splines. When the button 70 is pressed, splines on the skirt of button 70 engage with splines on the housing 10, preventing rotation of the button 70 (and hence the dose selector 80) during dispense. These splines disengage when the button 70 is released, allowing a dose to be dialled. Further, a ring of ratchet teeth is provided on the inner side of a button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The spring has a hook at one end for attachment on the number sleeve 60. A similar hook end is provided at the opposite end for attachment on the housing 10. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further.

The torsion spring 90 is formed from a helical wire with at least two different pitches. For example, both ends are formed from 'closed' coils, i.e. the pitch equals the wire diameter and each coil contacts the adjacent coil. The central portion has 'open' coils, i.e. the coils do not contact each other.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture 111 or window and two flanges extending on either side of the aperture. The flanges are preferably not transparent and thus shield or cover the number sleeve 60, whereas the aperture 111 or window allows viewing a portion of the number sleeve lower 60a. FIGS. 1 and 2 show the distal end 112 of one of these flanges, which is visible in window 11a of the housing 10. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate. The bearing 140 comprises a disc having a stem extending in the proximal direction. The stem has at its proximal end a convex contact surface. In addition, a recessed portion is provided on the stem. The curvature of the convex contact surface and the concave contact surface is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components.

A second embodiment of a threaded assembly is shown in FIGS. 3 to 8. For lucidity reasons, only three component parts of a drug delivery device are depicted in FIG. 3, namely a fixed housing tube 10', a nut 50' and a dial tube 60'. The fixed housing tube 10' is rotationally and axially constrained to the housing of the device. A splined interface 12, 51 on the inner bore of the fixed housing tube 10' and the outer surface of nut 50' rotationally constrains the last dose nut 50' whilst allowing axial translation.

During setting of a dose the dial tube 60' is rotated. As the dial tube 60' is rotated, the last dose nut 50' advances along a threaded path 61 on the dial tube 60' towards a rotational abutment, occurring at the proximal end of the threaded path 61. The last dose nut 50' does not rotate with the dial tube 60' due to its splined interface to the fixed housing tube 10'.

When the last dose nut 50' reaches the proximal end of the threaded path 61, a rotational abutment is created by rotational stops 52 of nut 50' and corresponding rotational stops 65 of dial tube 60' which rotationally couples the dial tube 60' to the fixed housing tube 10'. As the fixed housing tube 10' is rotationally constrained to the housing, the dial tube 60' also becomes rotationally constrained and the user is unable to increase the set dose. The length of the threaded path 61 on the dial tube 60' corresponds to the maximum number of doses that can be dispensed from the device. During dispensing, the dial tube 60' and fixed housing tube 10' do not rotate and, therefore, axial translation of the last dose nut 50' occurs only during dose setting. A last dose stop mechanism is created via interaction between the fixed tube of housing 10', the last dose nut 50' and the dial tube 60'.

The dial tube 60' may be axially constrained relative to the fixed housing tube 10', by other components (not shown), but may rotate relative to the fixed housing tube 10'. The dial tube 60' interfaces with the last dose nut 50' via a threaded interface on its outer surface which consists of three regions or portions with different thread leads. The thread 61 of dial sleeve 60' is provided with a distal (start) portion 62, a center portion 63 and a proximal (end) portion 64.

The thread lead at the start (distal portion 62) and end (proximal portion 64) of thread 61 of the dial tube 60' is greater (fast thread) than the central region 63 (slow thread). In addition, the fast threads 62, 64 are a twin-start form whereas the slow thread 63 is a single-start form. In this exemplary embodiment, the ratio between the fast and slow thread leads is 5:1, however, this exact ratio is not an absolute requirement.

The parallel flats on the outer surface of the threaded region of the dial tube 60' allow the last dose nut 50' to transition between the different thread regions and also permit simple "open and shut" moulding of the threaded region.

The form of the last dose nut 50' allows axial assembly onto the dial tube 60'. The twin-start fast thread is overhaulable such that the last dose nut 50' will rotate when it is pressed axially (while being allowed to rotate) during assembly until it reaches the assembly location feature. This feature prevents further last dose nut 50' rotation during assembly (under an axial force) but, during dialling, when a torque is applied to the last dose nut 50', this location feature is easily overcome to allow dialling to continue.

The inner surface of the last dose nut 50' has a number of discrete, equally spaced helical protrusions A, B, C and D which engage the dial tube 60' threads. These protrusions A, B, C and D are parts of a twin-start thread form with a lead equal to that of the fast thread portions 62, 64 of the dial tube thread 61.

In FIGS. 6 and 7 the thread protrusions A, B, C and D of last dose nut 50' are depicted engaged in the different thread region 62, 63 and 64 of dial tube 60' (shown with all but the thread protrusions of the last dose nut 50' cut away for clarity).

The thread protrusions A, B, C and D of the last dose nut 50' are arranged in two pairs (A and B on the one hand and C and D on the other hand) and each pair engages one of the two helices in the twin-start fast thread of distal portion 62. The ratio of thread lead between fast and slow portions is such that each last dose nut protrusion A, B, C and D fits in a different pitch when engaged with the slow thread 63.

These protrusions A, B, C and D are short enough in length to fit within the slow thread form 63 (which has increased thread form clearance) without interference even though the thread leads are unequal. The length of these thread protrusions A, B, C and D is a function of the ratio of thread leads and thread form clearance between fast and slow threads 62, 63, 64. As can be seen in FIGS. 6 and 7, the thread protrusions A, B, C and D are inclined with respect to the longitudinal axis of the assembly such that their slope allows them to be guided in fast thread portions 62, 64. Further, two opposite angles of the thread protrusions A, B, C and D are truncated (complanated) such that the slope of the truncated regions allows them to be guided in slow thread portion 63. In other words, different surfaces of the thread protrusions A, B, C and D guide the nut 50' on dial tube 60' depending on the different thread portions 62, 63, 64 engaging the thread protrusions A, B, C and D.

FIG. 6 shows a sequence of thread protrusion interactions as last dose nut 50' transfers from fast thread 62 to slow thread 63. The transition between different thread leads is critical to the function of this design. The rotational alignment between the end of the fast thread 62 to the start of the slow thread 63 dictates when the last dose nut 50' transfers from one thread to the next. This transition occurs abruptly and the thread arrangement ensures that at least one of the protrusions A, B, C and D of the last dose nut 50' is fully engaged with the dial tube 60' at all times. This improves robustness and last dose nut 50' positional reliability in impact or vibration conditions.

In step 1 of FIG. 6, last dose nut 50' is fully engaged with start fast thread 62. In step 2 only trailing protrusions B, D are engaged with the fast thread 62 with the last dose nut 50' guided by trailing protrusions B, D. In step 3 the leading protrusions A, C engage the start of slow thread 63. In step 4 the leading protrusions A, C are following slow thread 63 while trailing protrusions B, D are leaving fast thread 62. In step 5 the leading protrusions A, C continue to guide last dose nut 50' in slow thread 63 as the dial tube 60' is rotated until trailing protrusions B, D also engage slow thread 63.

FIG. 7 shows a sequence of thread protrusion interactions as the last dose nut 50' transfers from slow thread 63 to fast thread 64 and engages the last dose stops 52, 65. The last dose nut 50' transition from slow thread 63 to fast thread 64 occurs in a similar fashion to the transition from fast thread 62 to slow thread 63. Again, the leading protrusions A, C follow a different path to the trailing protrusions B, D and the parallel flat areas of the dial tube 60' permit the change of thread lead.

In step 1 of FIG. 7, the last dose nut 50' is engaged with slow thread 63 and guided by protrusions B, C and D. In step 2 last dose nut 50' is engaged with slow thread 63 and guided by protrusions B and D, while protrusion A enters fast thread 64. In step 3 the leading protrusion A engages the start of fast thread 64, while trailing protrusions B and D are leaving slow thread 63 as they reach the parallel flats on the dial tube 60'. In step 4 the leading protrusion A follows fast thread 64, while trailing protrusion B enters fast thread 64 and protrusions C and D are not interacting with thread 61 of dial tube 60'. In step 5 protrusions A and B follow fast thread 64, while protrusion C enters fast thread 64. In step 6 protrusions A and C with associated stop faces 52 on last dose nut 50' (not shown) contact rotational abutment 65 on dial tube 60' which prevents further dial tube rotation.

FIGS. 8a to 8f depict the sequence of movements of the last dose nut 50' and the dial tube 60' shown in FIG. 6 in a flat projection.

In an alternative embodiment, the roles of the fixed housing tube 10' and dial tube 60' can be reversed such that the fixed housing tube 10' is rotated during dose setting whilst the dial tube 60' is rotationally constrained to the housing. Both components may be rotationally fixed during dose dispensing.

In a further alternative embodiment, the last dose stop may also be achieved using the above mechanism altered so that the fixed housing tube 10' and the dial tube 60' rotate together during dose dispensing. In the same way as previously described, only the dial tube 60' rotates during dose setting. However if, during dispensing, both the fixed housing tube 10' and the dial tube 60' rotate together, at the same rate, no axial translation of the last dose nut 50' will be generated. The variation described in the above alternative embodiment, where the dial tube 60' and the fixed housing tube 10' perform opposite roles, may also be applied to this embodiment.

In a still further alternative, the dial tube 60' may comprise only one fast portion and only one slow portion of thread 61. The fast portion may be the distal portion 62 or the proximal portion 63.

All above mentioned embodiments of the present invention have the following advantages when compared to previous designs of last dose stop mechanisms: There are minimal axial space requirements since the majority of the last dose nut rotations are accommodated with a small lead thread. Further, proportionally large abutment faces are provided, relative to total axial length, since the thread pitch at the last dose stop condition is increased. Axial assembly of the last dose nut simplifies automated assembly. In addition, a face-to-face thread contact between last dose nut and a threaded carrier occurs when loaded in the last dose condition.

| Reference Numerals: | |
|---|---|
| 10 | outer housing |
| 10' | fixed housing tube |
| 11a | opening (window) |
| 11b | opening (window) |
| 12 | spline |
| 20 | cartridge holder |
| 30 | piston rod (lead screw) |
| 40 | drive sleeve |
| 50, 50' | nut |
| 51 | spline |
| 52 | rotational stop |
| 60 | dose setting element |
| 60' | dial tube |
| 61 | thread |
| 62 | (distal) fast portion |
| 63 | (central) slow portion |
| 64 | (proximal) fast portion |
| 65 | rotational stop |
| 70 | button |
| 80 | dose selector |
| 90 | torsion spring |
| 100 | cartridge |
| 110 | gauge element |
| 111 | opening |
| 112 | distal end |
| 120 | clutch |
| 130 | clutch spring |
| 140 | bearing |
| A, C | leading protrusion of nut 50' |
| B, D | trailing protrusion of nut 50' |

The invention claimed is:

1. An assembly for a drug delivery device comprising:
   a first threaded member,
   a second threaded member with a longitudinal axis and comprising a thread, the thread comprising at least two consecutive portions, the at least two consecutive portions having at least two different leads,
   wherein the first threaded member and the second threaded member are adapted and arranged to rotate with respect to one another about the longitudinal axis of the second threaded member during a dose setting operation of the assembly, and wherein the first threaded member is configured to be axially displaced along the second threaded member from a start position to an end position with respect to the second threaded member due to mechanical cooperation of the first threaded member with the thread during the dose setting operation,
   wherein the at least two consecutive portions of the thread comprise a fast portion and a slow portion,
   and wherein the fast portion of the thread comprises a greater lead than the slow portion of the thread, the fast portion of the thread comprises a multi-start thread, and the slow portion of the thread comprises fewer starts than the fast portion.

2. The assembly of claim 1, wherein the first threaded member is configured to engage the slow portion of the thread when the first threaded member is at the start position of the second threaded member and wherein the first threaded member is configured to engage the fast portion of the thread when the first threaded member is at the end position of the second threaded member.

3. The assembly of claim 1, wherein:
   the fast portion of the at least two consecutive portions of the thread comprise a first fast portion and a second fast portion, and
   the first threaded member is configured to engage the first fast portion of the thread when the first threaded member is at the start position of the second threaded member,
   the first threaded member is configured to engage the second fast portion of the thread when the first threaded member is at the end position of the second threaded member, and
   the first threaded member is configured to engage the slow portion of the thread when the first threaded member is at a center position of the second threaded member, the center position being located between the start position and the end position along the longitudinal axis of the second threaded member.

4. The assembly according to claim 1, wherein the multi-start thread of the fast portion of the thread is a twin-start thread, and the slow portion comprises a single-start thread.

5. The assembly according to claim 1, wherein the fast portion of the thread has a greater pitch than the slow portion of the thread, and a ratio of the lead of the fast portion of the thread to the lead of the slow portion of the thread is between 3:1 and 10:1.

6. The assembly according to claim 1, wherein the thread of the second threaded member terminates at the end position in a rotational hard stop.

7. The assembly according to claim 1, wherein the thread of the second threaded member comprises an assembly location feature at or near the start position.

8. The assembly according to claim 1, wherein:
   the slow portion of the thread comprises a single-start thread portion, and
   the first threaded member comprises at least a first thread form protrusion and a second thread form protrusion arranged such that the first and second thread form protrusions engage a same helical thread groove of the second threaded member when engaging the single-start thread portion and that the first and second thread form protrusions engage at least two different helical thread grooves of the second threaded member when engaging a multi-start thread portion of the second threaded member.

9. The assembly according to claim 8 wherein the first thread threaded member comprises a third thread form protrusion and a fourth thread form protrusion arranged such that the first and third thread form protrusions engage a first helical thread groove and the second and fourth thread form protrusions engage a second helical thread groove when engaging the multi-start thread portion of the of the second threaded member.

10. The assembly according to claim 1, comprising a third member adapted and arranged to axially guide the first threaded member and which is rotationally constrained to the first threaded member.

11. A drug delivery device for setting and dispensing a number of user variable doses of a medicament, the device comprising:
an assembly comprising:
a first threaded member,
a second threaded member with a longitudinal axis and comprising a thread, the thread comprising at least two consecutive portions, the at least two consecutive portions having at least two different leads,
wherein the first threaded member and the second threaded member are adapted and arranged to rotate with respect to one another about the longitudinal axis of the second threaded member during a dose setting operation of the assembly, and wherein the first threaded member is configured to be axially displaced along the second threaded member from a start position to an end position with respect to the second threaded member due to a mechanical cooperation of the first threaded member with the thread during the dose setting operation,
wherein the at least two consecutive portions of the thread comprise a fast portion and a slow portion, and
wherein the fast portion of the thread comprises a greater lead than the slow portion of the thread, the fast portion of the thread comprises a multi-start thread, and the slow portion of the thread comprises fewer starts than the fast portion; and
a cartridge containing a medicament.

12. The drug delivery device according to claim 11, comprising a housing, wherein the second threaded member and the housing are configured to rotate relative to each other during the dose setting operation and do not rotate relative to each other during a dose dispensing operation.

13. The drug delivery device according to claim 12, comprising a third member, wherein the third member is rotationally constrained to the housing or is a unitary part of the housing.

14. The drug delivery device according claim 11, wherein the second threaded member is a drive sleeve which is coupled to a piston rod and which is rotated with respect to a housing during the dose setting operation and which moves axially with respect to the housing during a dose dispensing operation.

15. The drug delivery device according to claim 11, comprising a third member, wherein the second threaded member is a dial sleeve which is coupled to a dose setting member and which is rotated with respect to the third member during the dose setting operation and which is not rotated relative to the third member during a dose dispensing operation.

* * * * *

UNITED STATES PATENT AND TRADEMARK OFFICE
CERTIFICATE OF CORRECTION

PATENT NO. : 10,702,659 B2
APPLICATION NO. : 15/517363
DATED : July 7, 2020
INVENTOR(S) : Anthony Paul Morris and Paul Roger Griffin Page 1 of 1

It is certified that error appears in the above-identified patent and that said Letters Patent is hereby corrected as shown below:

In the Claims

In Column 20, Line 57 (approx.), in Claim 9, delete "thread threaded" and insert -- threaded --, In Column 20, Line 62, in Claim 9, delete "of the of the" and insert -- of the --, In Column 22, Line 11, in Claim 14, after "according" insert -- to --.

Signed and Sealed this
Twenty-fifth Day of August, 2020

Andrei Iancu
*Director of the United States Patent and Trademark Office*